US005700913A

United States Patent [19]

Taniguchi et al.

[11] Patent Number: 5,700,913
[45] Date of Patent: *Dec. 23, 1997

[54] UNGLYCOSYLATED HUMAN INTERLEUKIN-2 POLYPEPTIDES

[75] Inventors: Tadatsugu Taniguchi, Tokyo; Masami Muramatsu, Tokorozawa; Haruo Sugano, Tokyo; Hiroshi Matsui, Yokohama; Nobukazu Kashima, Yokohama; Junji Hamuro, Yokohama, all of Japan

[73] Assignees: Ajinomoto Co., Inc.; Japanese Foundation for Cancer Research, both of Tokyo, Japan

[*] Notice: The term of this patent shall not extend beyond the expiration date of Pat. No. 5,399,669.

[21] Appl. No.: 331,146

[22] Filed: Oct. 28, 1994

Related U.S. Application Data

[63] Continuation of Ser. No. 99,003, Jul. 26, 1993, abandoned, which is a continuation of Ser. No. 561,531, Dec. 15, 1983, abandoned, which is a continuation-in-part of Ser. No. 463,496, Feb. 3, 1983, Pat. No. 4,738,927.

[30] Foreign Application Priority Data

| Dec. 15, 1982 | [JP] | Japan | 57-219518 |
| Dec. 24, 1982 | [JP] | Japan | 57-229619 |
| Dec. 27, 1982 | [JP] | Japan | 57-234607 |
| Dec. 29, 1982 | [JP] | Japan | 57-230371 |
| Dec. 29, 1982 | [JP] | Japan | 57-230372 |
| Feb. 3, 1983 | [EP] | European Pat. Off. | 83101035 |

[51] Int. Cl.$^6$ ............... C07K 14/55; C12N 15/26
[52] U.S. Cl. ............... 530/351; 424/85.2; 435/69.52; 435/252.8
[58] Field of Search ............... 530/351; 424/85.2; 435/69.52

[56] References Cited

U.S. PATENT DOCUMENTS

| 4,390,623 | 6/1983 | Fabricius et al. | 435/70.4 |
| 4,401,756 | 8/1983 | Gillis | 435/70.4 |
| 4,404,280 | 9/1983 | Gillis | 435/70.4 |
| 4,406,830 | 9/1983 | Fabricius et al. | 530/380 |
| 4,407,945 | 10/1983 | Gillis | 435/70.2 |
| 4,411,993 | 10/1983 | Gillis | 435/70.21 |
| 4,434,230 | 2/1984 | Ritts, Jr. | 435/7.24 |
| 4,490,289 | 12/1984 | Stern | 530/351 |
| 5,399,669 | 3/1995 | Taniguchi et al. | 530/351 |

FOREIGN PATENT DOCUMENTS 0088195  9/1983  European Pat. Off. .

OTHER PUBLICATIONS

Mier et al, *Proc. Natl.Acad. Sci. USA*, 77, 6134–6188 (1980).
Mier et al, *The Journal of Immunology*, 128, 1122 (1982).
Albert Lehninger, Biochemistry, The Johns Hopkins University School of Medicine, 226 (1970).

*Primary Examiner*—David L. Fitzgerald
*Attorney, Agent, or Firm*—Oblon, Spivak, McClelland, Maier & Neustadt, P.C.

[57] ABSTRACT

Recombinant human Interleukin-2 (IL-2) polypeptides are provided. The polypeptides are produced by expression of suitable nucleic acid molecules in transformed host cells such as *E. coli*.

5 Claims, 6 Drawing Sheets

FIG. 2A

ATCACTCTCTTAATCACTACTCACAGTAACCTCAACTCCTGCCACA ATG TAC AGG ATG CAA CTC CTG TCT TGC ATT GCA
                                                                1
                                                  Met Tyr Arg Met GlN Leu Leu Ser Cys Ile Ala
                    20                                                50

Leu Ser Leu Ala Leu Val Thr AsN Ser Ala Pro Thr Ser Ser Ser Thr Lys Lys Thr GlN Leu GlN Leu
CTA AGT CTT GCA CTT GTC ACA AAC AGT GCA CCT ACT TCA AGT TCT ACA AAG AAA ACA CAG CTA CAA CTG
                100                                                40

Glu His Leu Leu Leu Asp Leu GlN Met Ile Leu AsN Gly Ile AsN AsN T
GAG CAT TTA CTG CTG GAT TTA CAG ATG ATT TTG AAT GGA ATT AAT AAT TAC AAG AAT CCC AAA CTC ACC
150                                                250                              200
     60

Arg Met Leu Thr Phe Lys Phe Tyr Met Pro Lys Lys Ala Thr Glu Leu Lys His Leu GlN Cys Leu Glu
AGG ATG CTC ACA TTT AAG TTT TAC ATG CCC AAG AAG GCC ACA GAA CTG AAA CAT CTT CAG TGT CTA GAA
                                                                                                 80

Glu Glu Lys Pro Leu Glu Glu Val Leu AsN Leu Ala GlN Ser Lys AsN Phe His Leu Arg Pro Arg
GAA GAA CTC AAA CCT CTG GAG GAA GTG CTA AAT TTA GCT CAA AGC AAA AAC TTT CAC TTA AGA CCC AGG
                300                                                                                       350

Asp Leu Ile Ser AsN Ile AsN Val Ile Val Leu Glu Leu Lys Gly Ser Glu Thr Thr Phe Met Cys Glu
GAC TTA ATC AGC AAT ATC AAC GTA ATA GTT CTG GAA CTA AAG GGA TCT GAA ACA ACA TTC ATG TGT GAA
                                              120                                                                          400

FIG. 2B

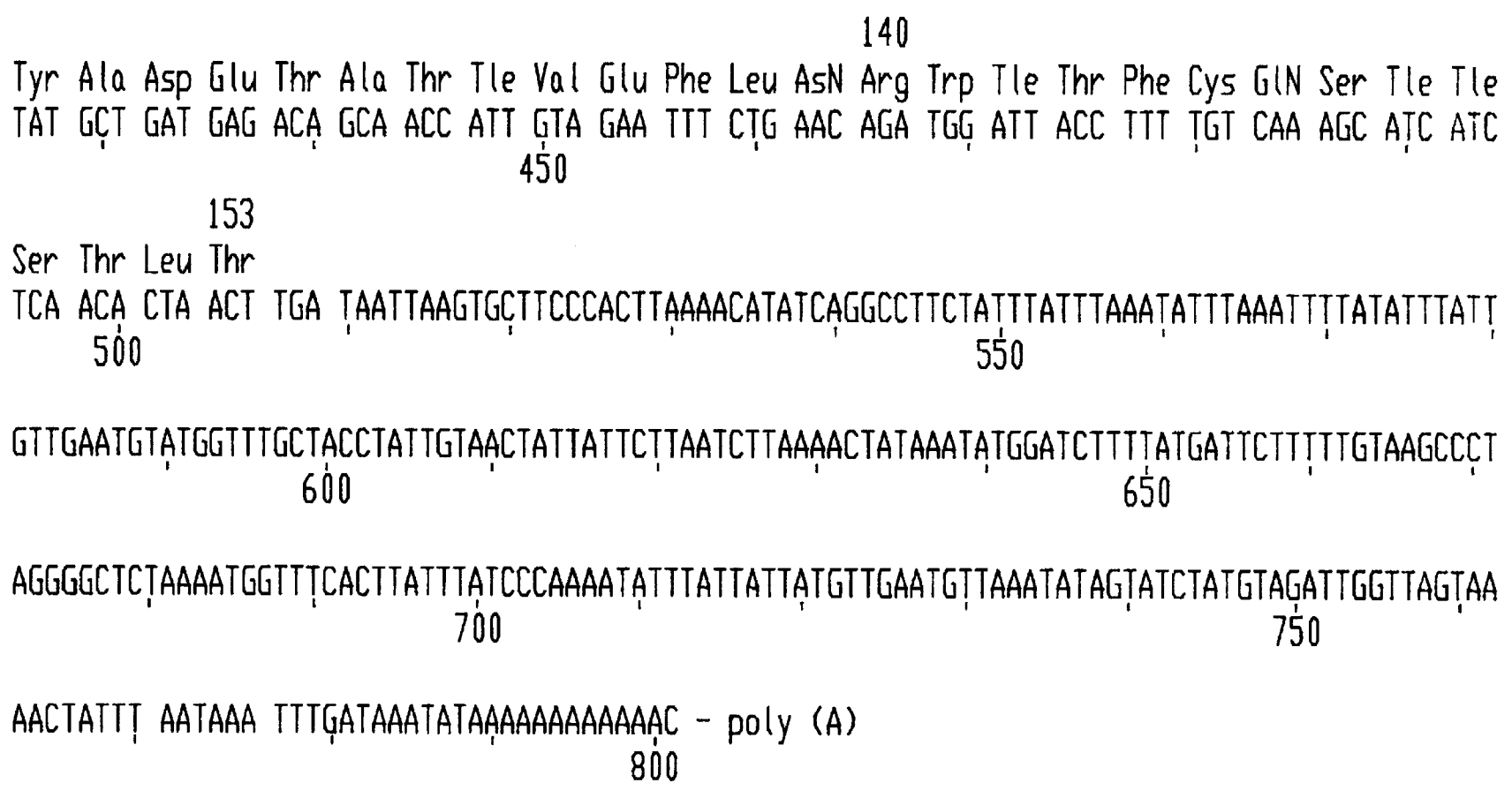

```
                                                                              140
Tyr Ala Asp Glu Thr Ala Thr Ile Val Glu Phe Leu Asn Arg Trp Ile Thr Phe Cys Gln Ser Ile Ile
TAT GCT GAT GAG ACA GCA ACC ATT GTA GAA TTT CTG AAC AGA TGG ATT ACC TTT TGT CAA AGC ATC ATC
                                              450
              153
Ser Thr Leu Thr
TCA ACA CTA ACT TGA TAATTAAGTGCTTCCCACTTAAAACATATCAGGCCTTCTATTTATTTAAATTTATATTTATT
            500                                          550

GTTGAATGTATGGTTTGCTACCTATTGTAACTATTATTCTTAATCTTAAAACTATATAAATATGGATCTTTATGATTCTTTTTGTAAGCCCT
                    600                                         650

AGGGGCTCTAAAATGGTTTCACTTATTTATCCCAAAATATTTATTATTTATGTTGAATGTTAAATATAGTATCTATGTAGATTGGTTAGTAA
                     700                                         750

AACTATTT AATAAA TTTGATAAATATAAAAAAAAAAAAAAAAAC - poly (A)
                                       800
```

UNGLYCOSYLATED HUMAN INTERLEUKIN-2 POLYPEPTIDES

This application is a Continuation of application Ser. No. 08/099,003, filed on Jul. 26, 1993, now abandoned which is a continuation of Ser. No. 06/561,531, filed on Dec. 15, 1983, now abandoned, which is a continuation-in-part of Ser. No. 06/463,496 filed Feb. 3, 1983 now U.S. Pat. No. 4,738,927.

BACKGROUND OF THE INVENTION

1. Field of the Invention

The present invention relates to interleukin-2 polypeptides.

2. Brief Description of the Prior Art

Interleukin-2 (hereinafter referred to as "IL-2"), formerly referred to as T cell growth factor, is a soluble protein, and is produced from T cells activated with a lectin or an antigen (Morgan, D. A. et al., Science, 193, 1007–1008 (1976), Gillis, S. et al., J. Immunol. 120, 2027–2033 (1978). Interleukin-2 (IL-2) is capable of modulating lymphocyte reactivity and promoting the in vitro long-term culture of antigen specific effector T-lymphocytes (Gillis, S. et al., Nature 268, 154–156 (1977)). IL-2 is also known to manifest other relevant biological activities such as enhancement of thymocyte mitogenesis (Chen, B. M. et al., Cell. Immunol., 22, 211–224 (1977), Shaw, J. et al., J. Immunol., 120 1967–1973, (1978)), induction of cytotoxic T cell reactivity (Wagner, H. et al., Nature, 284, 278–280 (1980)) and anti-SRBC plaque forming cell responses (Gillis, S., et al. J. Exp. Med., 149, 1960–1968 (1979)) in cultures of nude mouse spleen cells. Accordingly, this lymphocyte regulatory substance is useful in potentiating humoral and cellular immune responses and in restoring immune deficient state to a normal humoral and cellular immune state. These identified immunological activities of IL-2 indicate that IL-2 is useful for medical immunotherapy against immunological disorders including neoplastic diseases, bacterial or viral infections, immune deficient diseases, autoimmune diseases, etc. (Papermaster, B., et al., Adv. Immunopharm., 507 (1980)).

SUMMARY OF THE INVENTION

Now, new IL-2 polypeptides, which bear threonine as the C-terminal amino acid and no sugar moiety, have been found in the cells of *Escherichia coli*, which has been constructed by incorporation into a host of *Escherichia coli* of a recombinant DNA possessing a DNA fragment coding for IL-2 polypeptide.

BRIEF DESCRIPTION OF THE DRAWINGS

FIGS. 2A–B show the base sequence of the cloned gene.

Figure 1:
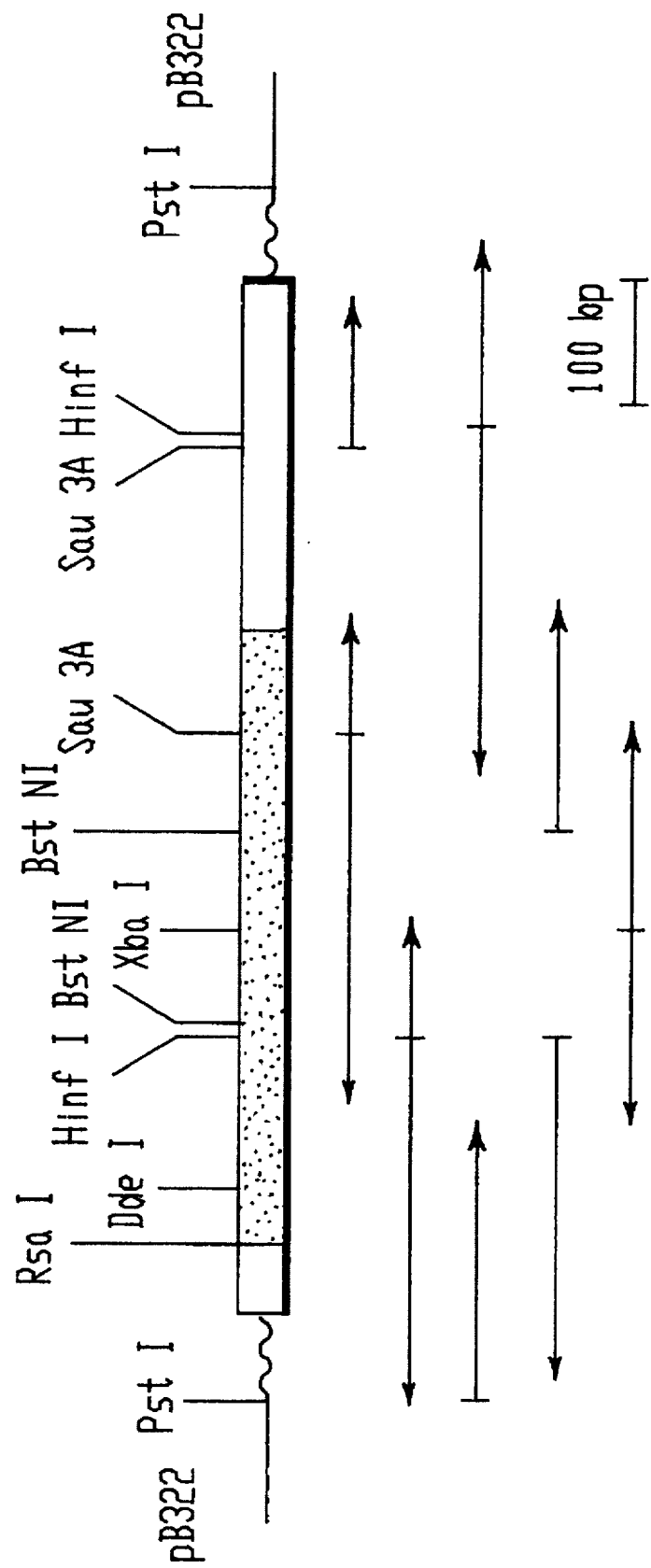
FIG. 1 shows a restriction endonuclease cleavage map of a cloned gene coding for IL-2 polypeptide.

In the figures, "A", "G", "C" and "T" represent deoxyadenylic acid, deoxyguanylic acid, deoxycytidylic acid and thymidylic acid, respectively.

BRIEF DESCRIPTION OF THE PREFERRED EMBODIMENT

The new IL-2 polypeptides of the present invention bear threonine as the C-terminal amino acid and no sugar moiety. One example of the IL-2 polypeptides has alanine as the N-terminal amino acid, and more precisely has the following amino acid sequence I (Formula I).

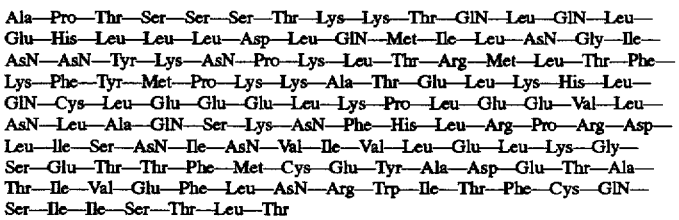

Another example of the IL-2 polypeptides has proline as the N-terminal amino acid, and more precisely has the following amino acid sequence II (Formula II).

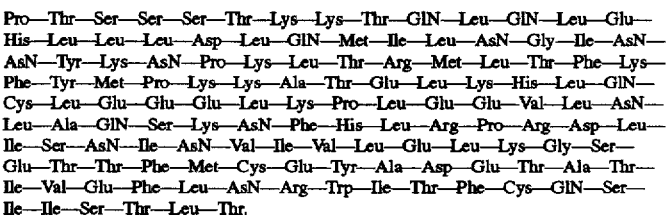

The IL-2 polypeptides of the present invention were produced in cells of *Escherichia coli* constructed by gene-recombination technique, by culturing the cells in a nutrient medium. Construction of *Escherichia coli* capable of producing the IL-2 polypeptides of the present invention was performed by the manner shown in Examples 1 and 2.

The IL-2 produced intracellularly or extracellularly is recovered by any known method, such as precipitation with ammonium sulfate, dialysis to remove salts (under normal or vacuum pressure), gel filtration, chromatography, preparative flat-bed iso-electric focusing, gel electrophoresis, high performance liquid chromatography (hereinafter "HPLC"), (ion exchange, gel filtration and reverse phase chromatography), and affinity chromatography on dye bound carrier, on activated Sepharose 4B coupled with monoclonal antibody against said IL-2 or on lectin bound Sepharose 4B and the like. Methods of recovery, and purification of IL-2, are described in Watson et al., J. Exp. Med., 150, 849–851 (1979), Gillis et al., J. Immunol., 124, 1954–1962 (1980), Mochizuki et al., J. Immunol. Methods, 39, 185–201 (1980), and Welte, K., et al., J. Exp. Med., 156, 454–464 (1982).

The activity of IL-2 may be ascertained by the microassay procedure principally discussed by Gillis et al. (Gillis, S., et al., J. Immunol., 120, 2027–2033 (1978)). The assay monitors the IL-2 dependent cellular proliferation of a cytotoxic T lymphocyte cell lines (hereinafter "CTLL") generated according to the methods described by Gillis et al., that is, $4 \times 10^3$ CTLL cells are inoculated into 100 μl of RMP1 1640 medium containing 2% FCS in 96 well flat-bottomed microplates together with 100 μl of the serially diluted translation products. After 20 hours incubation at 37° C. in 5% $CO_2$ incubator, cells were pulsed for 4 hours with 0.5 μCi of $^3$H-TdR, harvested onto glass fibre strips with the aid of an automated cell harvester and then the incorporated radioactivity is measured by liquid scintillation counting. By these assay procedures, the CTLL cells cultured in the presence of IL-2 were found to incorporate $^3$H-TdR in a dose dependent manner resulting in the definite calculation of the amount of IL-2 contained in test samples.

IL-2 possesses the activity to promote the proliferation of T lymphocytes, which enables the measurement of IL-2 activity using an index of T cell growth activity. That is, five CTLL cells are transferred into 100 μl of DMEM containing 2% FCS in 96 well flat-bottomed microplates together with 100 μl of the serially diluted translation products. After 72 to 96 hours incubation at 37° C. in a 5% $CO_2$ incubator, the number of cells grown and activated is counted under microscopy. As a positive external control group, 100 units/ ml, 10 units/ml of IL-2 are added and the IL-2 activity of the test sample is calculated in comparison with the number of grown viable cells in these control groups.

The polypeptide thus obtained shows the same biochemical and biological behavior as has been known for IL-2 produced by mammalian cells by mitogen stimulation, and has IL-2 activity. The molecular weight is around 15,000 dalton and IL-2 activity was completely neutralized or precipitated with monoclonal anti-IL-2 antibody in the presence or absence of immunoadsorbents, such as Igsorb (Enzyme Center). In immunoelectrophoresis, the IL-2 polypeptide shows only a single precipitate against the corresponding anti-IL-2 antibody. The IL-2 activity remains stable after reduction with 2-mercaptoethanol, and is resistant to treatment with DNAse and RNAse as well as to heat treatment at 56° C. for 30 min. The activity is stable at a pH between pH 2 to 9. The IL-2 produced could promote the growth of monoclonal functional T cells (cytotoxic T lymphocyte), enhance the thymocyte mitogenesis, give rise to the generation of anti-tumor specific cytotoxic T lymphocytes from memory state in the absence of the antigen, and could be used to augment natural killer cell activity against YAC-I and RLδ1 cells.

The IL-2 polypeptide preparations of the present invention are free from physiologically active substance produced by human cell, and can be more convenient for the therapeutic use than the known IL-2 polypeptide preparation produced by a human cell.

EXAMPLE 1

(1) Human T leukemia cell line, Jurkat cells (freely available in Japan, W. Germany and United States) were suspended in RPMI 1640 medium containing 10 vol/vol % FCS and were irradiated with X-ray till 10,000 roentgen at a room temperature for 50 seconds using X-ray irradiation apparatus Exs 150/300 - 4 (Toshiba, Japan), and thereafter the irradiated cell was cultured for 5 days at 37° C. in 5% $CO_2$ incubator at an initial cell density of $1 \times 10^5$ cells/ml in the culture medium mentioned above. The mutated cells (0.2 cells/well) were placed in wells 10 pieces of flat-bottomed microplates having 96 wells, and cultured at 37° C. in 5% $CO_2$ incubator for 21 days.

Clones obtained from the wells showing growth were repeatedly transferred into fresh culture medium to propagate the clone sizes, and the propagated clones were cultured for 24 hours at an initial cell density of $1 \times 10^6$ cells/ml in the presence of 50 μg/ml of Con. A and IL-2 activity was measured according to the methods aforementioned. Consequently, a human T cell line designated as Jurkat-111 (hereinafter "J-111") (ATCC CRL8129), cloned from parent Jurkat, was selected, of which productivity of IL-2 was increased 40 times as much as that of the parent strain. The cloned cell line J-111 could grow under conventional conditions and the growth rate shows almost the same with ordinary Jurkat cells.

(2) Cells ($1 \times 10^5$/ml) of J-111 were inoculated in 1,000 ml of serum free synthetic culture medium RITC 55-9 (Sato, T., et al., Exp. Cell Res., 138, 127–134 (1982)) in roller culture bottles (Falcon 3027) and cultured for 4 days at 37° C., and cells propagated were harvested by centrifugation. The harvested cells were again inoculated in the medium mentioned above which had been added with 25 μg/ml of Con. A to contain $4 \times 10^6$ cells/ml. In four batches of roller culture bottles (Falcon), 1,000 ml of the inoculated culture medium was placed into each batch. The cultivation was continued for 6 hours with rotating.

Jurkat cells ($1.2 \times 10^6$) thus stimulated with 25 μg/ml of Con. A for 6 hours were suspended in 8,000 ml of phosphate buffer balanced with saline (hereinafter "PBS"). The cells were washed twice by centrifugation and were resuspended in 800 ml of RSB solution (10 mM Tris HCl, pH 7.5, 10 mM NaCl, 1.5 mM $MgCl_2$) containing Ribonucleosides-Vanadyl Complex (10 mM), an inhibitor of nuclease. Then a detergent NP-40 was added to contain 0.05% as final concentration, followed by gentle mixing and the cell nuclei were removed by centrifugation for five minutes at 3,000 rpm at 4° C. SDS (0.5%) and EDTA (5 mM) were added to the supernatant and cytoplasmic RNA was extracted by addition of equal volume of phenol. After three times extraction with phenol, RNA was precipitated with two times volume of ethanol and precipitates were collected by centrifugation, which were solubilized in 10 mM Tris-HCl of pH 7.5. The amount of RNA obtained was 196 mg.

Fractionation of mRNA was carried out using affinity chromatography on oligo (dT)-Cellulose (P. L. Biochemicals, Type 7). An absorption solution was a solution of pH 7.5 containing 20 mM Tris-HCl, 0.5M NaCl, 1 mM EDTA and 0.5% SDS and elution was carried out with water and 10 mM Tris-HCl (pH 7.5) by turns after washing the column with the buffer (20 mM Tris-HCl, pH 7.5, 0.5M NaCl, 1 mM EDTA). The resultant mRNA eluted was 3.6 mg. Next, 2.4 mg of the mRNA obtained was fractionated by sucrose density gradient centrifugation (5 to 2.5% sucrose density gradient in a solution of pH 7.5 containing 50 mM Tris-HCl, 1 mM EDTA and 0.2M NaCl, centrifuged at 26,000 rpm for 24 hours at 4° C., and 11 to 12S fraction of mRNA was fractionated into fractions No. 12, 13, 14 in the amount of 50 μg, 46 μg and 60 μg, respectively.

(3) The mRNA obtained in fraction No. 13 was microinjected into the oocyte of *Xenopus laevis* (50 mg mRNA/egg)

and the culture supernatant was served for the assay of IL-2 activity. As shown in Table 1, the increase of the incorporation of $^3$H-TdR and the increase of number of activated T lymphocytes were confirmed, clearly verifying that mRNA in this fraction contains human IL-2 mRNA.

TABLE 1

(a)

| Sample | Dilution | Uptake of $^3$H-TdR (cpm) | Amount of IL-2* (unit/ml) |
|---|---|---|---|
| Control I (Medium for assay) | — | 553 | 0 |
| Control II (Supernatant of egg culture non-treated) | × 2 | 590 | 0 |
|  | × 32 | 572 |  |
| Translation product of fraction 13 | × 8 | 14,683 | 32 |
|  | × 32 | 10,165 |  |

(b)

| Sample | Dilution | Cell number of T-lymphocyte (No./well) | Amount of IL-2* (unit/ml) |
|---|---|---|---|
| Control I (Medium for assay) | × 2 | 0 | 0 |
|  | × 16 | 0 |  |
| Control II (Supernatant of egg culture non-treated) | × 2 | 0 | 0 |
|  | × 16 | 0 |  |
| Translation product of fraction 13 | × 2 | 115 | 40 |
|  | × 16 | 55 |  |

*The unit was calculated by comparing the amount of incorporated $^3$H-TdR with that of standard IL-2 (10 unit/ml) according to probit analysis.

(4) Thereafter cDNA was synthesized in vitro from No. 13 fraction of 11 to 12S mRNA containing IL-2 mRNA and recombinant DNA was constructed with the plasmid vector pBR 322. With the recombinant DNA, *Escherichia coli* was transformed, and clone acquired IL-2 cDNA clones was selected, as follows:

Fifty mM Tris-HCl buffer (pH 7.5), 30 mM NaCl, 6 mM MgCl$_2$, 5 mM dithiothreitol (hereinafter "DTT"), 0.5 mM of each dATP, dGTP, dCTP, dTTP (dCTP contained $^{32}$P radiolabelled one), 0.7 µg oligo (dT)$_{10}$, 10 µg mRNA and 15 unit AMV reverse transcriptidase (J. W. Beard) were mixed and maintained for 90 min. at 41° C.

After termination of the reaction, DNA was recovered as ethanol precipitates after the phenol treatment, and DNA was solubilized in a solution of pH 7.5 containing 20 mM Tris and 1 mM EDTA.

Two point five µg of ss-cDNA was synthesized. To remove mRNA present in this solution, the solution was made 0.33 N-NaOH by addition of NaOH, allowed to stand for 15 hours at a room temperature, then the solution was neutralized with equal volume of 1M-Tris-HCl of pH 7.5 and passed through "Sephadex G-50" column. The recovered cDNA was 1.8 µg.

Fifty mM phosphate buffer (pH 7.5), 10 mM MgCl$_2$, 10 mM DTT, 0.75 mM of each dATP, dGTP, dCTP, dTTP (dCTP contains $^3$H radiolabelled one), 1.8 µg ss-cDNA, and 8 unit of polymerase I (BRL, United States) were mixed and were allowed to react for 15 hrs. at 15° C. After the termination of the reaction, DNA was recovered as ethanol precipitate, after treatments with phenol and with chloroform. 1.10 µg of ds-cDNA was generated. A mixture of 50 mM sodium acetate (pH 4.5), 0.2M NaCl, 1 mM ZnCl$_2$ and 1.10 µg of ds-cDNA was incubated for 20 min. at 37° C., added with 0.25 unit of nuclease S$_1$ (Sankyo, Japan), and incubated further for 15 min.

After the termination of the reaction, the reaction product treated twice with phenol was applied onto Sephadex G-50 to get 0.55 µg of ds-cDNA.

A mixture of 0.14M potassium cacodylate, 30 mM Tris base, 0.1 mM Dtt, 1 mM COCl$_2$, 0.64 mM $^{32}$P-dCTP (spc. act. 2.7×10$^6$ cpm/n mol), 0.55 µg of ds-cDNA and 5 unit of terminal transferase (BRL) were incubated for 7 min. at 37° C., then applied onto Sephadex G-50 column after phenol treatment to get 0.50 µg DNA as ethanol precipitates. The recovered DNA was found to be extended with around 50 dCMP residues at the both 3' terminus.

Ten µg of pBR 322 DNA was cleaved with restriction enzyme PstI, and 3'-termini of the cleaved DNA were added with dGMP chain, by the same method as that used in the addition of dCMP to ds-cDNA mentioned above, except dGTP was used in place of dCTP.

(5) A mixture of 50 mM Tris-HCl (pH 7.5), 0.1M NaCl, 5 mM EDTA, 0.05 µg of pBR 322 elongated with dGMP residues and 0.01 µg of cDNA extended with dCMP was incubated firstly for 2 min. at 65° C., then for 120 min. at 46° C., for 60 min. at 37° C. and finally for 60 min. at a room temperature. *E. coli* χ 1776 (Curtiss III, R., et al., in Molecular Cloning of Recombinant DNA, (W. A. Scott & R. Werner ed.) Academic Press (1977)) was inoculated in 50 ml of L broth containing 100 µg/ml of diaminopimelic acid, 50 µg/ml of thymidine, 1% tryptophan, 0.5% yeast extract, 0.5% NaCl and 0.1% glucose and cultured in shaking at 37° C. until the absorbance of culture liquid at 562 nm became around O.D. 0.3. After the termination of the culture, the culture liquid was left at 0° C. for 30 min., then the bacterial cells were collected by centrifugation followed by twice washing with 25 ml of a solution containing 5 mM Tris-HCl (pH 7.6), 0.1M NaCl, 5 mM MgCl$_2$ and 10 mM RbCl.

Cells thus obtained were suspended in 20 ml of a solution containing 5 mM Tris-HCl (pH 7.6), 0.25M KCl, 5 mM MgCl$_2$, 0.1M CaCl$_2$ and 10 mM RbCl and were left at 0° C. for 25 min., then cells were collected to resuspend them into 1 ml of the same solution, the recombinant DNA described above was added into 0.2 ml of the cell suspension and the suspension was left at 0° C. for 60 min. Then 0.7 ml of L broth was added to culture medium (0.1 ml) was thoroughly spread on the surface of 1.5% agarose medium composed of L broth containing 100 µg/ml diaminopimelic acid, 50 µg/ml thymidine and 15 µg/ml tetracycline, and incubated at 37° C. for two days.

Four hundred and thirty two colonies appeared were divided into 18 groups, each containing 24 different bacterial clones, inoculated in 200 ml of L-broth containing 100 µg/ml of diaminopimelic acid, 50 µg/ml of thymidine and 10 µg/ml of tetracycline and cultured in shaking at 37° C. for 5 to 7 hrs. Then, 200 ml of fresh L-broth containing chloramphenicol at a final concentration of 170 µg/ml was added to culture further overnight. Thus amplified plasmid DNA was purified according to a conventional mean. Clones possessing IL-2 cDNA were screened by a mRNA hybridization-translation assay (hereinafter "H-T assay"). H-T assay here employed was carried out as follows: Purified DNA (25 µg) was cleaved with restriction enzyme Hind III, treated with phenol three times, treated with phenol-chloroform and with chloroform, respectively, precipitated with ethanol, washed with 80% ethanol and dissolved in 40 µl of 80% formamide. The reaction mixture was heated for denaturation at 90° C. for 5 min., then diluted to 1.3 ml with 10 x SSC (1.5M NaCl, 0.15M sodium citrate). The DNA was thereafter fixed onto nitrocellulose filters, which filters were dried up at 80° C. for 3 hrs. and incubated for 18 hrs. at 37° C. in the solution containing 50% formamide, 20 mM Pipes of pH 6.5, 0.75M NaCl, 5 mM EDTA, 0.2% SDS and 250 μg of poly (A) mRNA from induced J-111 cells to hybridize the DNA fixed on filters with IL-2 mRNA. Then the filters were washed at 65° C. three times with solution consisting of 10 mM Pipes of pH 6.5, 0.15M NaCl, 1 mM Pipes, 10 mM NaCl solution and treated with 0.5 mM EDTA, 0.1% SDS solution at 95° C. for 1 min. to recover the hybridized mRNA from the filters. Thus extracted mRNA was purified on oligo dT-Cellulose column according to the conventional methods and injected into Xenopus oocytes to determine the IL-2 activity of translated proteins. One out of 18 groups, each consisting of 24 clones, gave positive 48 unit/ml IL-2 activity in $^3$H-TdR incorporation assay described previously, while others being clearly negative. Then 24 single colonies belonging to the positive group were inoculated in 200 ml of L-broth possessing the same composition described, cultured aerobically for 5 to 7 hrs. at 37° C. and similarly chloramphenicol containing fresh L-broth was further added. After amplification of plasmid DNA by an overnight culture, plasmid DNA was similarly purified according to the standard procedures. After cleavage of about 5 μg of each plasmid DNA with Hind III, each plasmid DNA was bound to nitrocellulose filters similarly. The filters were hybridized with IL-2 mRNA and hybridized mRNA was recovered to inject into Xenopus oocyte to determine the IL-2 activity of translated proteins. As shown in Table 2, only plasmid DNA purified from a single colony, designated as p3-16, gave the positive IL-2 activity. Therefore this clone was identified as the clone possessing IL-2 DNA (*E. coli* χ 1776/p3-16 AJ 11995 (FERM-BP-225)). Thus plasmid DNA, p3-16, was confirmed to share exactly the DNA (IL-2 gene) capable of forming the specific hybrid with IL-2 mRNA.

TABLE 2

(a)

| Sample | Dilution | Uptake of $^3$H-TdR (cpm) | Amount of IL-2* (unit/ml) |
|---|---|---|---|
| Control I (Medium for assay) | — | 2,010 | 0 |
| Control II (Supernatant of culture liquid of non-treated egg) | × 2 | 2,120 | 0 |
| | × 32 | 2,482 | |
| Translation product of mRNA | × 2 | 20,453 | 58 |
| | × 32 | 20,961 | |

(b)

| Sample | Dilution | Cell number of T-lymphocyte (No./well) | Amount of IL-2* (unit/ml) |
|---|---|---|---|
| Control I (Medium for assay) | — | 0 | 0 |
| Control II (Supernatant of culture liquid of non-treated egg) | × 2 | 0 | 0 |
| | × 32 | | |
| Translation product of mRNA | × 2 | 88 | 32 |
| | × 32 | 42 | |

*mNRA hybridized with cDNA from plasmid p3-16.

(6) The cDNA insert of plasmid p3-16 showed characteristics to be cleaved by restriction enzyme XbaI at a single site and by BstNI at two sites, (at upstream and downstream of XbaI cleavage site). However, the plasmid p3-16 contained a cDNA insert consisting of about 650 base pairs, which apparently correspond to a part of IL-2 mRNA of 11 to 12S size.

Therefore another cDNA library were prepared according to the procedure of Land et al. (Land et al., Nucleic Acids Res., vol 9, p2251, (1981)) using IL-2 mRNA as a template. Single stranded cDNA (1.6 μg) was synthesized by using 4 μg of IL-2 mRNA elongated by dCMP residues, and ds-cDNA was synthesized by using oligo (dG)$_{12-18}$ as the primer for DNA polymerase I (Klenow fragment). The cDNA (0.6 μg) longer than 680-base pair DNA size marker was obtained by a sucrose gradient centrifugation and inserted into the PatI site of pBR 322 by the standard G-C tailing method. After transformation of *E. coli* X 1776 by the recombinant DNA, approximately 2,000 colonies were screened by in situ hybridization method of Grunstein-Hogness with nick-translated p3-16 cDNA insert as the probe and the colony containing plasmid pIL 2-50A containing around 850 base pairs and the transformed clone (*E. coli* X 1776/pIL 2-50A, AJ 11996 (FERM-BP-226)) were identified. A restriction endonuclease cleavage maps of the cDNA insert of pIL 2-50A are shown in FIG. 1. To isolate a gene coding for IL-2 peptide from transformed *E. coli* X 1776 pIL 2-50A, plasmid DNA was digested with restricted enzyme PstI after isolation of DNA region from the cells according to the conventional means. Thus produced smaller fragment among generated two DNA fragments was DNA gene coding for IL-2 peptide. The complete nucleotide sequence of the PatI insert from pIL 2-50A was determined by the procedure of Maxam and Gilbert (Maxam, A. W. et al., Enzym. 65, 499–560, 1980), and the whole structure is shown in FIGS. 2A–B.

Figure 3:
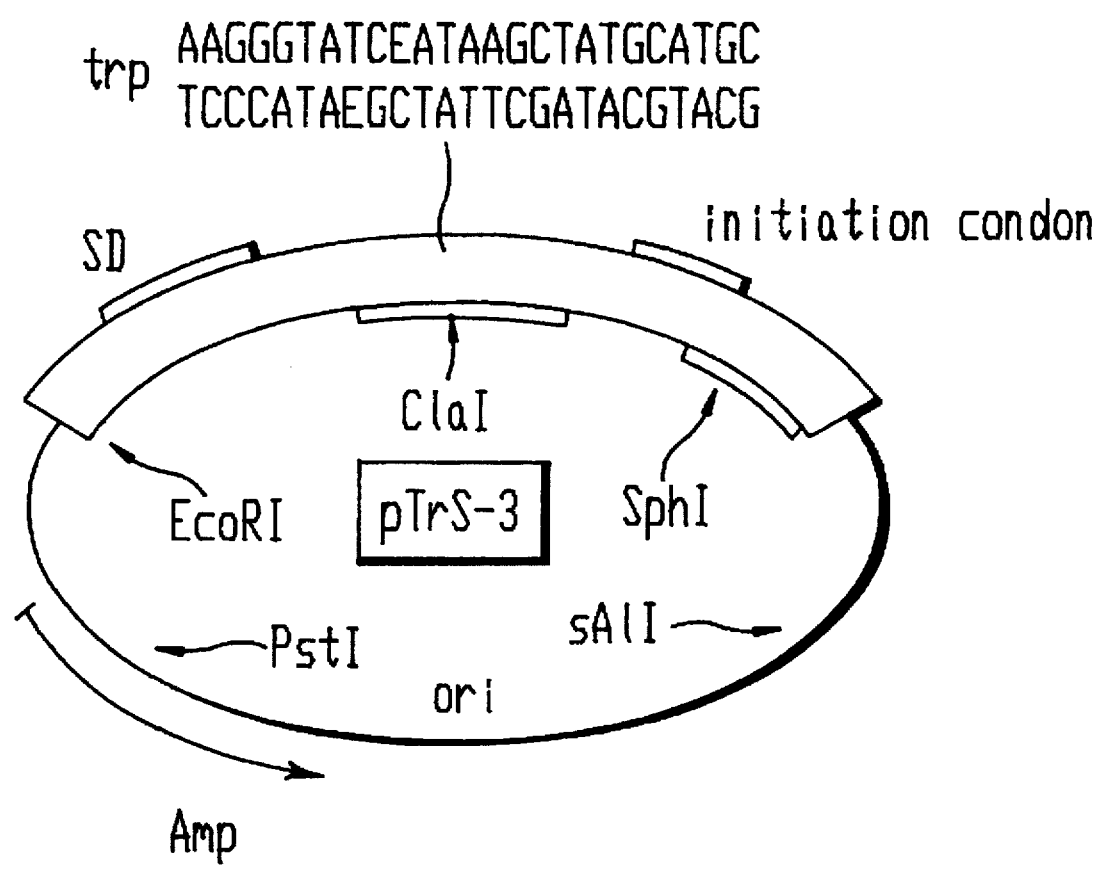
FIG. 3 shows the plasmid vector pTrS-3.
Figure 4:
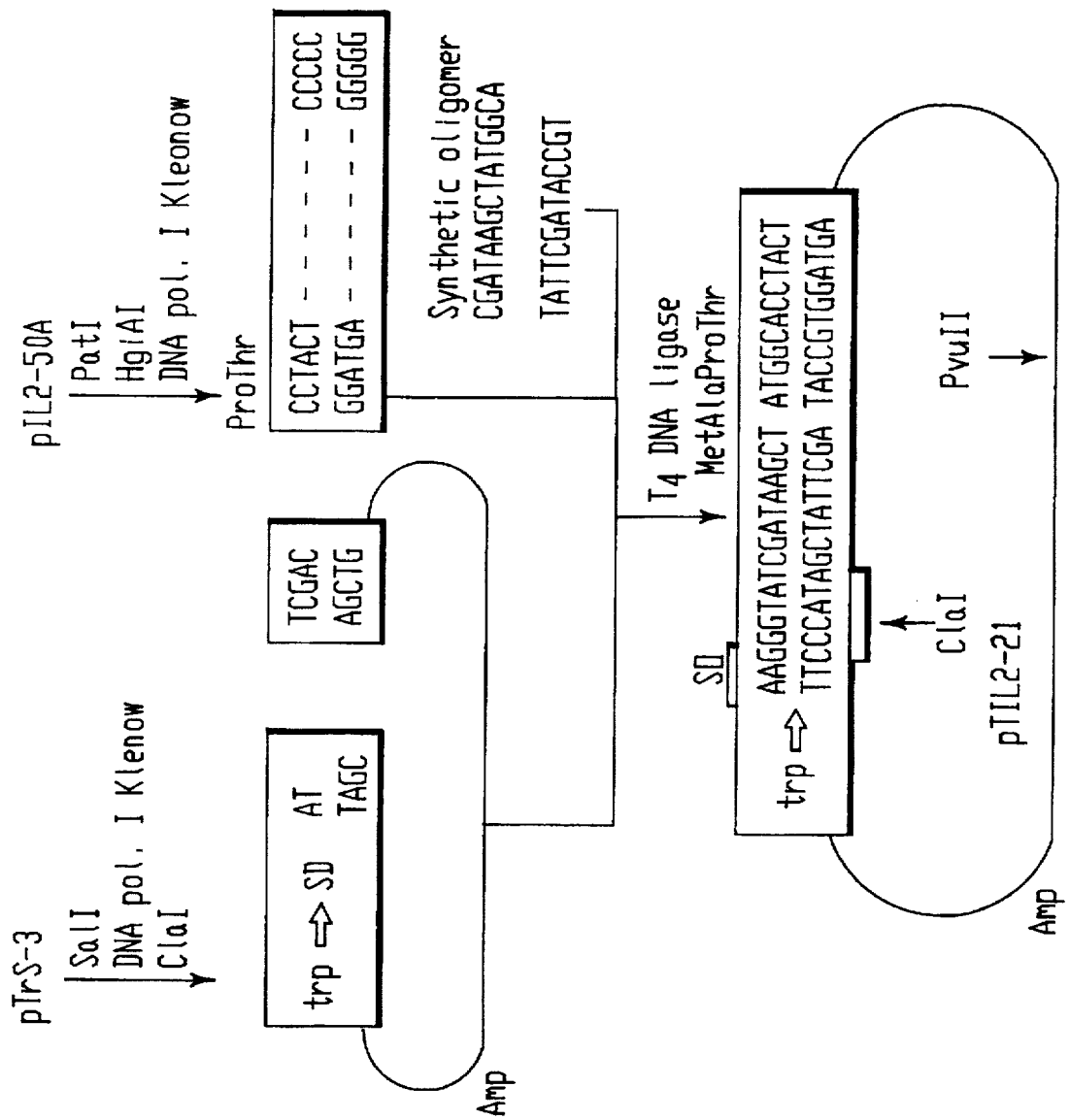
FIG. 4 is a flowchart showing the construction of recombinant DNA pTIL2-21.

(7) A plasmid which should direct the synthesis of human IL-2 in *E. coli* cells was constructed as follows. A plasmid pTIL 2-21 was constructed from PtrS-3 (Nishi T., Taniguchi T. et al., SEIKAGAKU 53, 967, (1981)), of which restriction map is shown in FIG. 3, and pIL 2-50A containing the IL-2 cDNA by the manner illustrated in FIG. 4. Plasmid pTrS-3 include insertion of the region of Trp promoter and Shine Dalgarno (hereinafter "SD") between EcoRI site and ClsI site of pBR 322.

Plasmid pTrS-3 (10 μg) was at first cleaved with the restriction enzyme SalI and the SalI site was rendered flush by the treatment with DNA polymerase (Klenow fragment) or with T4 DNA polymerase. After cleavage with ClaI, a larger fragment, containing the trp promoter region, was isolated by agarose gel electrophoresis in a conventional manner to recover 3 μg of DNA.

On the other side, 11 μg of pIL 2-50A insert into PstI was cleaved with HgiA1, treated with T4 DNA polymerase and a larger fragment was isolated and purified by agarose gel electrophoresis. Thus cDNA fragment coding for 132 amino acids of IL-2 was obtained in an amount of 7.2 μg. Then 0.45 μg of the fragment containing a trp promoter (described above), 0.5 μg of HgiA1-PstI fragment containing IL-2 and synthetic oligonucleotides (5') CGATAAGCTATGGCA (3'), and (3') TATTCGATACCGT (5') (each 20 pmole), both of which were phosphorylated at 5'-terminus, were lignated with 1.0 unit of T4 DNA ligase in 66 mM Tris-HCl of pH 7.5 containing 6.6 mM MgCl$_2$: 1 mM ATP and 10 mM DTT, and the mixture was allowed to react at 4° C. overnight.

Thus ligated plasmid was then used to transform *E. coli* HB101. Among the transformants appeared on L broth agar plate containing ampicillin, the target transformants were selected as follows. The candidate transformants able to hybridize with both of IL-2 cDNA and synthetic oligonucleotides were firstly selected by colony hybridization method, then the transformants processing the insertion of DNA fragment initiating from CCT sequence at position 111 to 113 in FIG. 2A (CCTACT - - - ) just downstream of ATG GCA sequence were selected by PstI, XbsI cleavage. The *E. coli* HB101 containing pTIL2-21a or PTIL2-21b was cultured under the conventional conditions known for the propagation of microorganisms. The cells were grown in 10 ml of X broth (2.5% Bactotrypton, 1.0% yeast extracts, 0.1% glucose, 20 mM MgSO$_4$, 50 mM Tris-HCl, pH 7.5) containing 25 µg/ml streptomycin and 25 µg of ampicillin at 37° C. for an overnight. One ml of the culture suspension was inoculated into the same X broth (100 ml) and cultured at 37° C. When O.D at 650 mµ arrived around 1.5–2.0, 3-indole acrylic acid (IAA) was added. Three hours after the addition of inducer, the cells were collected, washed with 20 mM-Tris-HCl (pH 7.5, 30 mM NaCl) and resuspended into 8 ml of the same buffer. For the efficient functioning of Trp promoter inducers such as IAA was added at a final concentration of 50 µg/ml. Thus produced proteins in bacterial cells were extracted by sonication (0° C., 2 min,) or lysozyme (8 µg) digestion (0° C., 20 min.) followed with three successive freeze-thawing. According to this procedure IL-2 was usually extracted from organisms. The extracted IL-2 activity ranged from 10,000 to 120,000 units/ml. *Escherichia coli* HB101 possessing pTIL2-21a (AJ12013) and *Escherichia coli* HB101 possessing pTIL2-21b (AJ12014) have been deposited in the assession numbers of FERM-SP248 and FERM-BP249 respectively.

(8) *Escherichia coli* AJ12013 (FERM-BP248) was inoculated on 10% of an L medium (containing 1% tryptophan, 0.5% yeast extract, 0.5% NaCl and 0.1% glucose) containing 25 µg/ml of ampicillin and 25 µg/ml of streptomycin and cultured. When optical density at 650 nm reached about 1.0, 3-indol-acrylic acid was added to the medium at a concentration of 50 µg/ml and cells were collected 2 hours after. After washing the cells with a 20 mM Tris buffer (pH 7.5) containing 30 mM MaCl, the cells were again suspended at 180 ml of the same buffer solution. Then, 20 ml of a lysozyme solution and further 2 ml of 0.5M EDTA (pH 8.0) were added to the suspension. Thereafter, the mixture was allowed to stand for 20 minutes at 0° C. By subsequently performing freezing-thawing at −50° C. and 37° C. 3 times, the cells were disrupted. Ultra centrifugation was carried out at 30,000 rpm for 30 minutes to obtain an extract of the cells for the disrupted cells.

Out of the extract 160 ml (total protein content 2.4 g, IL-2 activity $3\times10^5$ µ/ml, specific activity $2\times10^4$ µ/mg) was passed through a column (32 mm diameter×65 mm) filled up with 50 ml of porous glass beads (CPG-10, pore size 350 angstrom, 120–200 mesh, manufactured by Electro-Nucleonics Co., Ltd.) which had been previously equilibrated with a 0.1M tris-(hydroxymethyl)aminomethane-hydrochloric acid buffer solution of pH 7.7 containing 0.2M sodium chloride to adsorb IL-2 thereto. Thereafter, the column was washed with 100 ml of the aforesaid buffer solution and then IL-2 was eluted out with 200 ml of a 0.1M tris(hydroxymethyl)aminomethanehydrochloric acid buffer solution of pH 7.7 containing 0.75M potassium thiocyanate.

After dialyzing 150 ml of the obtained IL-2 eluate to a 0.07M acetic acid-sodium acetate buffer solution having pH 6.0 for 48 hours, the eluate was passed through a column (22 mm diametric×105 mm) filled up with 40 ml of "CM-Sephadex C-25" (manufactured by Pharmacia Co., Ltd.) which had been previously equilibrated with the same buffer solution to adsorb IL-2 thereto. After subsequently washing the column with 100 ml of the same buffer solution, the adsorbed IL-2 was eluted out with 100 ml of a 0.5M acetic acid-sodium acetate buffer solution of pH 6.0.

Solid ammonium sulfate was added to 80 ml of the obtained eluate to render 80% saturation. After settling overnight, formed precipitates were collected by centrifugation and dissolved in 10 ml of a 0.05M phosphoric acid-sodium phosphate buffer solution having pH 7.0 and containing 1.25M sodium chloride. Using 500 ml of "Sephadex G-75 Super File" (manufactured by Pharmacia Co., Ltd.) equilibrated with the same buffer solution, gel filtration (32 mm diameter×65 cm) was performed. IL-2 was eluted out as a single active peak at a molecular weight of 14,000 to 16,000 daltons.

Glucose was added to 20 ml of the obtained IL-2 fraction so as to have the final concentration of 1M, and the mixture was passed through a column (10 mm diameter×6 cm) filled up with 5 ml of "Phenyl Sepharose C1-6B" (manufactured by Pharmacia Co., Ltd.) previously equilibrated with a 0.05M phosphoric acid-sodium phosphate buffer solution having pH 7.0 and containing 1.25M sodium chloride and 1M glucose to adsorb IL-2 thereto. Next, the column was washed with 15 ml of the same buffer solution. Thereafter the adsorbed IL-2 was eluted out with 30 ml of a 0.05M phosphoric acid-sodium phosphate buffer solution having pH 7.0 and containing 0.1M sodium chloride and 1M glucose.

Using a Hitachi 638-30 high speed liquid chromatography apparatus (manufactured by Hitachi Ltd.), 5 ml out of 20 ml of the obtained IL-2 fraction was passed through a column (4.6 mm diameter×75 mm, manufactured by Beckman Co., Ltd.) for high speed liquid chromatography filled up with "Ultrapore RPSC", which had been previously equilibrated with a 0.5M acetic acid-triethylamine buffer solution of pH 4.0, at a flow rate of 0.5 ml/min. Thereafter, elution was performed using the aforesaid buffer solution (hereafter referred to as Solvent A) and an 80% v/v 1-propanol aqueous solution (hereafter referred to as Solvent B).

Solvent A alone was flow for the initial 10 minutes; during 20 to 22 minutes, solvents were flown by varying from 100% Solvent A to 70% Solvent A+30% Solvent B according to the linear gradient method; and the solvents were flown down during 22 to 86 minutes by varying from 70% Solvent A+30% Solvent B to 30% Solvent A+70% Solvent B according to the linear gradient method. Detection of proteins was performed by measuring the absorbance at 280 nm using a wavelength variable ultraviolet absorbance monitor, Hitachi 638-41 (manufactured by Hitachi Ltd.). Human IL-2 was eluted out as a single peak 70 minutes after from the initiation of the elution. The recovery rate from the extract of the bacteria was 30%. The thus obtained IL-2 showed an activity of $5\times10^7$ units per 1 mg of the protein.

(9) The obtained IL-2 showed a single band at the location of a molecular weight of about 16,000 daltons by SDS-polyacrylamide gel electrophoresis. The analysis of the N-terminal residue was conducted in a conventional manner by the dansyl method and as a result, only alanine was detected as the N-terminal amino acid.

Next, using about 40 µg (250 picomoles) of the obtained IL-2, the amino acids constituting IL-2 were sequentially determined from the N-terminal by the automatic Edman (degradation) method (*The Journal of Biological Chemistry*, vol. 256, pages 7990–7997, 1981) using a Gaseous Phase Protein Sequencer Model 470A (manufactured by Applied Biosystems Co., Ltd.). The decomposition product at a first step was analyzed by a high speed liquid chromatography, where 200 picomoles of PTH-alanine was detected but other PTH-amino acids were not detected. Thus, the N-terminal amino acid of IL-2 was identified to be alanine. From the decomposition product at a second step, 180 picomoles of PTH-proline and a small quantity of PTH-alanine were detected but no other PTH amino acids were detected; thus, a second amino acid from the N-terminal of IL-2 was identified as proline. From the decomposition product at a third step, 30 picomoles of PTH-threonine and a small quantity of PTH-proline were detected but no other PTH-amino acids were detected; thus a third amino acid from the N-terminal of IL-2 was identified as threonine. It is known that PTH-threonine is unstable and liable to be decomposed; a low recovery rate of PTH-threonine is often experienced in the art. From the decomposition products from 4th, 5th, 6th and 7th steps, 20 to 40 picomoles of PTH-serine, PTH-serine, PTH-serine and PTH-threonine were exclusively detected, respectively. It is known that PTH-serine is also unstable and liable to be decomposed and for this reason, the recovery rate was poor but no other PTH-amino acids were detected; thus, the 4th to 7th amino acids from the N-terminal of IL-2 were identified as serine, serine, serine and threonine, respectively. From the decomposition products at 8th, 9th and 10th steps, 100 picomoles of PTH-lysine, 120 picomoles of PTH-lysine and 20 picomoles of PTH-threonine were detected, respectively and the 8th, 9th and 10th amino acids from the N-terminal of IL-2 were identified as lysine, lysine and threonine, respectively. In a similar fashion, the 11th to 15th amino acids from the N-terminal of IL-2 were identified as glutamine, leucine, glutamine, leucine and glutamic acid respectively, whereby the detected data of the corresponding PTH amino acids were 60 to 120 picomoles.

From the decomposition product at a 16th step, 20 picomoles of PTH-histidine were detected. It is known that PTH-histidine is also poor in the recovery rate. In a similar fashion, from the decomposition products at 17th to 30th from the N-terminal of IL-2 were identified as leucine, leucine, leucine, aspartic acid, leucine, glutamine, methionine, isoleucine, leucine, asparagine, glycine, isoleucine, asparagine and asparagine, respectively. The partial amino acid sequence of IL-2 is fully identical with that anticipated by the base sequence of gene.

Next, the C-terminal amino acid of IL-2 obtained was determined. The determination of the C-terminal was performed in a manner similar to the method of Chang et al using carboxypeptidase Y (Biochem. J., 199, 547–555 (1981)). In 30 μl of a 0.05M acetic acid buffer solution (pH 5.4) was dissolved about 80 μg (500 picomoles) of IL-2 and 1 μl of a 0.1 mg/ml solution of carboxypeptidase Y was added to the solution and the resulting mixture was maintained at 25° C. From the reaction liquid, 7 μl each of samples was taken with the lapse of time. After freeze drying each of the samples, 10 μl of a 0.1M NaHCO$_3$ (adjusted pH to 9.0) was added thereto. Next, 20 μl of a 4 mmole/μ acetone solution of dimethylaminoazobenzenesulfonyl chloride purified from recrystallization was added. After heating the mixture at 70° C. for 15 minutes, 200 μl out of the mixture, HPLC analysis was performed. As a result of the HPLC analysis, dimethylaminoazobenzenesulfonyl (hereafter simply referred to as DABS)-threonine was detected from the reaction liquid at the initial stage and DABS-leucine was detected somewhat later; thus, the C-terminal amino acid of IL-2 was identified as threonine and the amino acid sequence around the C-terminal as leucine-threonine (C-terminal).

From the above experimental results, it was found that the amino acid sequences around the N-terminal and C-terminal of IL-2 obtained were completely identical with those anticipated from the base sequence of a gene and the compositional ratio of the constituent amino acids was then examined.

In a conventional manner about 40 μg (250 picomoles) of IL-2 was hydrolyzed in 6N HCl at 110° C. for 48 hours and the analysis was conducted using an amino acid analyzer. The results are shown in the table. With respect to serine, threonine and tryptophan which are known to cause decomposition under the hydrolysis conditions described above, serine and threonine were corrected using the analytical data of hydrolysis at 110° C. for 24 hours, and tryptophan was separately determined by fluorometry. As is evident from Table 3, the amino acid composition of IL-2 obtained was identical with that expected from the base sequence of a gene. From the above results, it is judged that a primary structure of IL-2 obtained would be as shown in the amino acid sequence of Formula L

TABLE 3

| Compositional Ratio of Amino Acid | | |
|---|---|---|
| | Found Value | Assumed Value |
| Aspartic acid | 12.5 | 12 |
| Threonine | 12.5 | 13 |
| Serine | 7.7 | 8 |
| Glutamic acid | 18.4 | 18 |
| Proline | 5.2 | 5 |
| Glycine | 2.1 | 2 |
| Alanine | 5.0 | 5 |
| ½ Cystine | 2.7 | 3 |
| Valine | 4.1 | 4 |
| Methionine | 4.3 | 4 |
| Isoleucine | 8.6 | 9 |
| Leucine | 21.5 | 22 |
| Tyrosine | 2.9 | 3 |
| Phenylalanine | 5.8 | 6 |
| Lysine | 11.3 | 11 |
| Histidine | 3.2 | 3 |
| Tryptophane | 1.0 | 1 |
| Arginine | 4.1 | 4 |

The structure of IL-2 was further confirmed by measuring the molecular weights of two kinds of decomposition products of IL-2 by means of mass spectrometry. Fifteen micrograms of IL-2 (about 1 nmole) was dissolved in 14 μl of 70% formic acid, added with 46 μg of cyanogen bromide, which cleaves a carboxyside of methionine residue and the methionine is converted to homoserine or homoserine lactone, in 1 μl of 70% formic acid, and then allowed to stand overnight at a room temperature. The reaction mixture was evaporated in vacuo, added with 40 μg of water, and then lyophilized. The product was added with 14 μl of 1% ammonium bicarbonate and then digested with 0.3 μg of trypsin (Warthington Co.,), to cleave a carboxyside of lysine or arginine residue, in 0.6 μl of 1% ammonium bicarbonate at 37° C. One third aliquot of the reaction mixture was withdrawn after 3 hr. or 6 hr. incubation, added with 0.5 μl of acetic acid, and then subjected to mass spectrometry. Another 15 μg of IL-2 was also treated by the same method as mentioned above except digesting with 0.3 μg of Staphylococcus aureus D8 protease (Miles Co.), to cleave carboxyside of glutamic acid residue, instead of trypsin. Molecular weights of the decomposition products in a mixture state were measured by means of fast atom bombardment mass spectrometry on a JMS-HX100 spectrometer (JEOL Co.). Many kinds of molecular ion peaks accompanied by isotopic peaks were observed on mass spectra.

Representative peaks corresponding to the molecular weights (NH⁺) of cyanogen bromide-trypsin decomposition products of IL-2 are shown in Table 4.

TABLE 4

| Molecular Weight | Identification |
| --- | --- |
| m/z 1783 | Lys-9 to Hse-23 |
| m/z 1665 | Thr-10 to Hse-23 |
| m/z 1049 | Ile-24 to Lys-32 |
| m/z 389 | Leu-36 to Arg-38 |
| m/z 508 | Leu-40 to Lys-43 |
| m/z 561 | Ala-50 to Lys-54 |
| m/z 2564 | His-55 to Lys-76 |
| m/z 939 | Asn-77 to Arg-83 |
| m/z 1583 | Asp-84 to Lys-97 |
| m/z 1874 | Cys-105 to Arg-120 |

Representative peaks corresponding to the molecular weights (MH⁺) of cyanogen bromide-V8 protease decomposition products of IL-2 are shown in Table 5.

TABLE 5

| Molecular Weight | Identification |
| --- | --- |
| m/z 1619 | Ala-1 to Glu-15 |
| m/z 952 | His-16 to Hse-23 |
| m/z 1859 | Ile-24 to Hse-39 |
| m/z 919 | Leu-40 to Hse-46 |
| m/z 1241 | Leu-53 to Glu-62 |
| m/z 857 | Glu-61 to Glu-67 or Glu-62 to Glu-68 |
| m/z 728 | Glu-62 to Glu-67 or Glu-63 to Glu-68 |
| m/z 3116 | Val-69 to Glu-95 |
| m/z 633 | Thr-111 to Glu-116 |

Above data show that 83% of the primary structure of IL-2 was identified (Ala-1 to Met-46, Ala-50 to Lys-97 and Cys-105 to Arg-120; i.e., 110 amino acid residues in 133 amino acid residues of IL-2) by mass spectrometry, ascertaining the primary structure of IL-2 of the amino acid sequence of Formula I.

EXAMPLE 2

Figure 5:
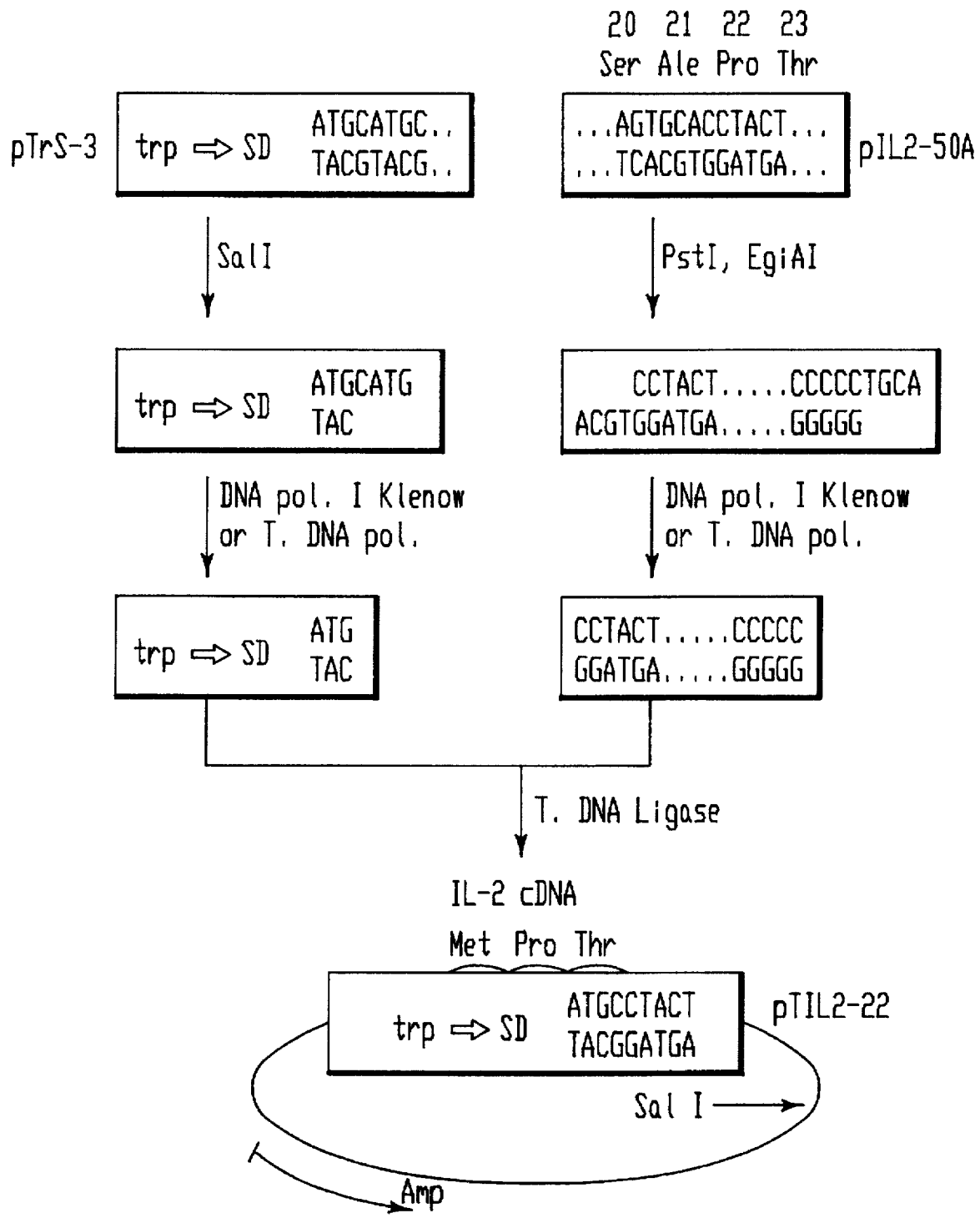
FIG. 5 is a flowchart showing the construction of a recombinant DNA pTIL2-22.

(1) A plasmid which should direct the synthesis of human IL-2 in *E. coli* cells was constructed as follows. A plasmid pTIL2-22 was constructed from pTrS-3 (Nishi T., Taniguchi, T. et al), SEIKAGAKU 53, 967, (1981)), a pIL 2-50A containing the IL-2 cDNA by a series of modification procedures as illustrated in FIG. 5. A plasmid pTrS-3 include insertion of the region of Trp promoter and Shine Dalgarno (hereinafter "SD") between EcoRI site and ClaI site of pBR 322. The plasmid also contains an ATG initiation codon 13 bp downstream of the SD sequence as well as a single SphI site as illustrated in FIG. 3. The vector is very efficient to produce the said protein when DNA sequence corresponding to the said protein is inserted in phase just downstream of the ATG codon, which is generated by SphI digestion and by subsequent treatment by T4 DNA polymerase of pTrS-3). Therefore the plasmid pTrS-3 (30 μg) was cleaved with a restriction enzyme SphI in a conventional manner and after successive treatment with phenol and chloroform, ethanol precipitates were recovered, then both ends were rendered flush by the treatment of T4 DNA polymerase. Then the DNA (21.4 μg) was recovered by similar successive phenol, chloroform treatment and ethanol precipitation. On the other side, 380 μg of pIL 2-50A containing an IL-2 cDNA was cleaved by PstI and then IL-2 cDNA insert was isolated by agarose gel electrophoresis. cDNA insert (11 μg) was cleaved by HgiAI, treated by T4 DNA polymerase and 10 μg of the DNA of larger site was isolated by agarose gel electrophoresis. According to the procedures of cDNA (7.2 μg) coding for 132 amino acids was obtained and this DNA fragment had blunt ends (FIG. 5). Then the thus obtained cDNA fragment ligated to a pTrS-3 vector, previously digested by SphI and treated by T4 DNA polymerase just downstream of ATG sequence. Thus ligated plasmid was then used to transform into *E. coli* HB101 according to the conventional procedures. Ligation was carried out as follows. IL-2 cDNA (0.4 μg) larger fragment and 0.2 μg of pTrS-3) vector DNA were mixed with 0.8 unit of T4 DNA ligase in 66 mM Tris-HCl of pH 7.5 containing 6.6 mM MgCl₂, 1 mM ATP and 10 mM DTT, and the mixture was allowed to react at 4° C. overnight. Among the transformants appeared on L broth agar plate containing ampicillin, colonies containing the IL-2 cDNA portion, which encodes 132 amino acids were selected by in situ colony hybridization assay. Thus selected colonies were cultured (10 ml) again to prepare plasmid DNA by lysozyme treatment and by freeze thawing. The plasmid DNAs were cleaved with PstI and XbaI, and the resulting products were analyzed by agarose gel electrophoresis in order to identify pTIL 2-22 in which the cDNA was linked to the ATG sequence of pTrS-3 in correct orientation. The *E. coli* HB101 containing pTIL 2-22 was cultured under the conventional conditions known for the propagation of microorganisms. The cells were grown in 10 ml of X broth (2.5% Bactotrypton, 1.0% yeast extracts, 0.1% glucose, 20 mM MgSO₄, 50 mM Tris-HCl, pH 7.5) containing 25 μg/ml streptomycin and 25 μg of ampicillin at 37° C. for an overnight. One ml of the culture suspension was inoculated into the same X broth (100 ml) and cultured at 37° C. When optical density at 650 mμ arrived around 1.5–2.0, 50 μg.ml 3-indole acrylic acid (IAA) was added to the medium. Three hours after the addition of the inducer, the cells were collected, washed with 20 mM Tris-HCl (pH 7.5, 30 mM NaCl) and resuspended into 8 ml of the same buffer. Thus produced proteins in bacterial cells were extracted by sonication (0° C. 2 min.) followed with three successive freeze-thawing. The extracted IL-2 activity ranged from 10,000 to 120,000 units/ml.

*E. coli* HB101 containing pTIL 2-22 (AJ12009) has been deposited in the accession number of FERM-BP245.

(2) *E. coli* AJ12009 was cultured by the manner shown in step (8) of Example 1. A homogenate of the cell obtained contained 1×10⁵ u/ml of IL-2 activity, and from 160 ml of the homogenate by the manner shown in step (8) of Example 1, IL-2 polypeptide was recovered in the recovery yield of 20%, obtaining IL-2 preparation having about 5×10⁷ units per 1 mg of IL-2 protein.

The obtained IL-2 polypeptide preparation showed a single band at the location of a molecular weight of about 16,000 daltons by SDS-polyacrylamide gel electrophoresis.

(3) Using 20 μg of the obtained IL-2, the amino acids constituting IL-2 were sequentially determined from the N-terminal by the method shown in step (9) of Example 1, and found proline as the first N-terminal amino acid and threonine as the second N-terminal amino acid.

Third to twentieth amino acids from the N-terminal proline were also found by the manner shown in step (9) of Example 1 as Ser, Ser, Ser, Thr, Lys, Lys, Thr, GlN, Leu, GlN, Leu, Glu, His, Leu, Leu, Leu, Asp, and Leu.

C-terminal amino acid of the IL-2 preparation obtained was also determined by the manner shown in step (9) of Example 1, and was threonine.

The structure of IL-2 was further confirmed by measuring the molecular weights of decomposition products of IL-2 by means of mass spectrometry according to the same method as in step (a) of Example 1. Similar results were obtained except for observation of a peak at m/z 1548 (corresponding to Pro-1 to Glu-14) instead of m/z 1619 on the mass spectrum of cyanogen bromide-V8 protease decomposition product.

From the above results, it is judged that a primary structure of IL-2 obtained would be as shown in the amino acid sequence of Formula II.

What is claimed as new and is desired to be secured by Letters Patent of the United States is:

1. A substantially purified, unglycosylated recombinant polypeptide having the amino acid sequence of a human interleukin-2 (IL-2) protein, wherein said human IL-2 protein is encoded by a mRNA molecule present in a human cell which will hybridize to a DNA probe having the coding sequence of the cDNA sequence shown in FIG. 2 in a solution of 50% formamide, 20 mM PIPES, pH 6.5, 0.75M NaCl, 5 mM EDTA, and 0.2% SDS at 37° C. for 18 hours followed by washing three times at 65° C. in a solution of 10 mM PIPES, pH 6.5, 0.15M NaCl, and wherein said polypeptide possesses a biological IL-2 activity by promoting the proliferation of cytotoxic effector T lymphocytes in vitro.

2. A substantially purified, unglycosylated recombinant polypeptide which has an activity of IL-2 in promoting the growth of cytotoxic T lymphocytes, and which has the primary structure:

Ala—Pro—Thr—Ser—Ser—Ser—Thr—Lys—Lys—Thr—Gln—Leu—Gln—
Leu—Glu—His—Leu—Leu—Leu—Asp—Leu—Gln—Met—Ile—Leu—Asn—
Gly—Ile—Asn—Asn—Tyr—Lys—Asn—Pro—Lys—Leu—Thr—Arg—Met—
Leu—Thr—Phe—Lys—Phe—Tyr—Met—Pro—Lys—Lys—Ala—Thr—Glu—
Leu—Lys—His—Leu—Gln—Cys—Leu—Glu—Glu—Glu—Leu—Lys—Pro—
Leu—Glu—Glu—Val—Leu—Asn—Leu—Ala—Gln—Ser—Lys—Asn—Phe—
His—Leu—Arg—Pro—Arg—Asp—Leu—Ile—Ser—Asn—Ile—Asn—Val—
Ile—Val—Leu—Glu—Leu—Lys—Gly—Ser—Glu—Thr—Thr—Phe—Met—
Cys—Glu—Tyr—Ala—Asp—Glu—Thr—Ala—Thr—Ile—Val—Glu—Phe—
Leu—Asn—Arg—Trp—Ile—Thr—Phe—Cys—Gln—Ser—Ile—Ile—Ser—
Thr—Leu—Thr.

3. A substantially purified, unglycosylated recombinant polypeptide which has an activity of IL-2 in promoting the growth of cytotoxic T lymphocytes, and which has the primary structure:

Pro—Thr—Ser—Ser—Ser—Thr—Lys—Lys—Thr—Gln—Leu—Gln—Leu—
Glu—His—Leu—Leu—Leu—Asp—Leu—Gln—Met—Ile—Leu—Asn—Gly—
Ile—Asn—Asn—Tyr—Lys—Asn—Pro—Lys—Leu—Thr—Arg—Met—Leu—
Thr—Phe—Lys—Phe—Tyr—Met—Pro—Lys—Lys—Ala—Thr—Glu—Leu—

Lys—His—Leu—Gln—Cys—Leu—Glu—Glu—Glu—Leu—Lys—Pro—Leu—
Glu—Glu—Val—Leu—Asn—Leu—Ala—Gln—Ser—Lys—Asn—Phe—His—
Leu—Arg—Pro—Arg—Asp—Leu—Ile—Ser—Asn—Ile—Asn—Val—Ile—
Val—Leu—Glu—Leu—Lys—Gly—Ser—Glu—Thr—Thr—Phe—Met—Cys—
Glu—Tyr—Ala—Asp—Glu—Thr—Ala—Thr—Ile—Val—Glu—Phe—Leu—
Asn—Arg—Trp—Ile—Thr—Phe—Cys—Gln—Ser—Ile—Ile—Ser—Thr—
Leu—Thr.

4. A substantially purified, unglycosylated recombinant polypeptide which has an activity of IL-2 in promoting the growth of cytotoxic T lymphocytes, and which has the primary structure:

Met—Ala—Pro—Thr—Ser—Ser—Ser—Thr—Lys—Lys—Thr—GlN—Leu—GlN—Leu—
Glu—His—Leu—Leu—Leu—Asp—Leu—GlN—Met—Ile—Leu—AsN—Gly—Ile—AsN—
AsN—Tyr—Lys—AsN—Pro—Lys—Leu—Thr—Arg—Met—Leu—Thr—Phe—Lys—Phe—
Tyr—Met—Pro—Lys—Lys—Ala—Thr—Glu—Leu—Lys—His—Leu—GlN—Cys—Leu—
Glu—Glu—Glu—Leu—Lys—Pro—Leu—Glu—Glu—Val—Leu—AsN—Leu—Ala—GlN—
Ser—Lys—AsN—Phe—His—Leu—Arg—Pro—Arg—Asp—Leu—Ile—Ser—AsN—Ile—
AsN—Val—Ile—Val—Leu—Glu—Leu—Lys—Gly—Ser—Glu—Thr—Thr—Phe—Met—
Cys—Glu—Tyr—Ala—Asp—Glu—Thr—Ala—Thr—Ile—Val—Glu—Phe—Leu—AsN—
Arg—Trp—Ile—Thr—Phe—Cys—GlN—Ser—Ile—Ile—Ser—Thr—Leu—Thr.

5. A substantially purified, unglycosylated recombinant polypeptide which has an activity of IL-2 in promoting the growth of cytotoxic T lymphocytes, and which has the primary structure:

Met—Pro—Thr—Ser—Ser—Ser—Thr—Lys—Lys—Thr—Gln—Leu—Gln—Leu—Glu—
His—Leu—Leu—Leu—Asp—Leu—Gln—Met—Ile—Leu—Asn—Gly—Ile—Asn—Asn—
Tyr—Lys—Asn—Pro—Lys—Leu—Thr—Arg—Met—Leu—Thr—Phe—Lys—Phe—Tyr—
Met—Pro—Lys—Ala—Thr—Glu—Leu—Lys—His—Leu—Gln—Cys—Leu—Glu—
Glu—Glu—Leu—Lys—Pro—Leu—Glu—Glu—Val—Leu—Asn—Leu—Ala—Gln—Ser—
Lys—Asn—Phe—His—Leu—Arg—Pro—Arg—Asp—Leu—Ile—Ser—Asn—Ile—Asn—
Val—Ile—Val—Leu—Glu—Leu—Lys—Gly—Ser—Glu—Thr—Thr—Phe—Met—Cys—
Glu—Tyr—Ala—Asp—Glu—Thr—Ala—Thr—Ile—Val—Glu—Phe—Leu—Asp—Arg—
Trp—Ile—Thr—Phe—Cys—Gln—Ser—Ile—Ile—Ser—Thr—Leu—Thr.

\* \* \* \* \*

UNITED STATES PATENT AND TRADEMARK OFFICE
CERTIFICATE OF CORRECTION

PATENT NO. : 5,700,913
DATED : DECEMBER 23, 1997
INVENTOR(S) : TADATSUGU TANIGUCHI ET AL.

It is certified that error appears in the above-identified patent and that said Letters Patent is hereby corrected as shown below:

Column 9, line 31, "FERM-SP248" should read --FERM-BP248--.

Column 10, line 41, "was flow for" should read --was flown for--.

Signed and Sealed this

Twenty-first Day of July, 1998

Attest:

BRUCE LEHMAN

Attesting Officer     Commissioner of Patents and Trademarks